United States Patent [19]

Batzer et al.

[11] 4,227,005

[45] * Oct. 7, 1980

[54] DIALCOHOLS

[75] Inventors: Hans Batzer, Arlesheim; Jürgen Habermeier, Pfeffingen; Daniel Porret, Fresens, all of Switzerland

[73] Assignee: Ciba-Geigy AG, Basel, Switzerland

[*] Notice: The portion of the term of this patent subsequent to Dec. 21, 1988, has been disclaimed.

[21] Appl. No.: 956,523

[22] Filed: Oct. 31, 1978

Related U.S. Application Data

[63] Continuation of Ser. No. 541,911, Jan. 17, 1975, Pat. No. 4,161,594, which is a continuation-in-part of Ser. No. 82,074, Oct. 19, 1970, abandoned, which is a continuation-in-part of Ser. No. 870,547, Nov. 4, 1969, Pat. No. 3,629,263.

[30] Foreign Application Priority Data

Nov. 11, 1968 [CH] Switzerland ............... 16803/68

[51] Int. Cl.³ .......................................... C07D 233/74
[52] U.S. Cl. .................................................. 548/312
[58] Field of Search ..................................... 548/312

[56] References Cited

U.S. PATENT DOCUMENTS

| | | | |
|---|---|---|---|
| 2,211,001 | 8/1940 | Chwala | 548/352 |
| 2,890,132 | 6/1959 | Howsmon | 106/165 |
| 3,018,246 | 1/1962 | Hughes et al. | 548/352 |
| 3,088,948 | 5/1963 | Little et al. | 544/221 |
| 3,216,957 | 11/1965 | Krumm | 548/352 |
| 4,161,594 | 7/1979 | Batzer et al. | 548/312 |

OTHER PUBLICATIONS

Gabriel et al. Berichte 1917, vol. 50, pp. 817–825.
Ishii et al. J. Chem Soc. (Japan) Ind. Chem. Section, 1958, vol. 61, pp. 1254–1257.
Kirk-Othmer Encyclopedia of Chemical Technology 2nd ed. vol. 6, pp. 482–484. N. Y., Wiley, 1965.
Morton Laboratory Technique in Organic Chemistry pp. 148–149. N. Y., McGraw-Hill, 1938.
Sadtler Standard Spectra Infrared Prism No. 32939 Philadelphia, Sadtler, 1967.
Weissberger Technique of Organic Chemistry vol. III, Part I Separations and Purification pp. 395–398. N. Y., Interscience, 1953.
Woellner et al. Chem Abst. 1970, vol. 73, No. 109783r.
Wolf et al. Chem. Abst. 1970, vol. 73, No. 57,285h.

*Primary Examiner*—Henry R. Jiles
*Assistant Examiner*—Jane T. Fan
*Attorney, Agent, or Firm*—Joseph F. DiPrima; Harry Falber

[57] ABSTRACT

New dialcohols of mononuclear, five-membered or six-membered, unsubstituted or substituted N-heterocyclic compounds which contain two NH-groups in the molecule, by reaction of mononuclear, five-membered or six-membered, unsubstituted or substituted N-heterocyclic compounds, for example hydantoin, barbituric acid, uracil, dihydrouracil, parabanic acid and the corresponding derivatives, with ethylene oxide or propylene oxide to give dialcohols. These diols are useful as intermediates for the preparation of polymers, such as polyesters or polyurethanes, or of epoxy resins.

1 Claim, No Drawings

DIALCOHOLS

This is a continuation of application Ser. No. 541,911 filed on Jan. 17, 1975, Now U.S. Pat. No. 4,161,594, which is a continuation-in-part of application Ser. No. 82,074, filed Oct. 19, 1974, now abandoned, which is a continuation-in-part of application Ser. No. 870,547 filed Nov. 4, 1969, now U.S. Pat. No. 3,629,263.

The subject of the present invention are dialcohols of the general formula

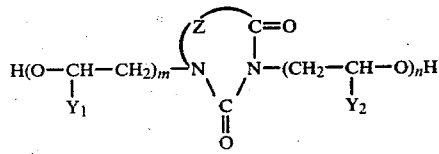

wherein $Y_1$ and $Y_2$ each denote a hydrogen atom or a methyl group and Z denotes a nitrogen-free, divalent residue which is required for the completion of a five-membered or six-membered, unsubstituted or substituted, heterocyclic ring, and m and n each denote an integer having a value of 1 to 30, preferably of 1 to 4.

The residue Z in formula (I) preferably consists only of carbon and hydrogen or of carbon, hydrogen and oxygen. It can for example be a residue of formulae

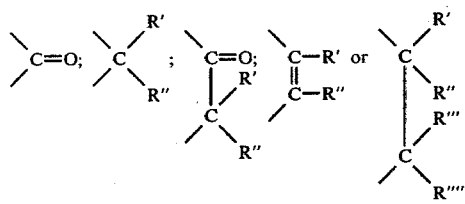

wherein R', R", R''' and R'''' independently of one another can each denote a hydrogen atom or, for example, an alkyl residue, an alkenyl residue, a cycloalkyl residue, or an optionally substituted phenyl residue.

The new dialcohols of formula (I) can be manufactured by reacting mononuclear N-heterocyclic compounds of the general formula

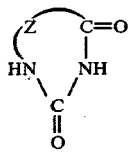

wherein Z has the same significance as in formula (I), with alkene oxides, preferably ethene oxide (ethylene oxide) or propene oxide (propylene oxide) and preferably in the presence of a suitable catalyst.

The addition of an alkene oxide to both NH-groups of the N-heterocyclic compounds of formula (II) can be carried out in the presence of acid or alkaline catalysts, with a slight excess of equivalent epoxide groups of the alkene oxide being employed per equivalent NH- group of the N-heterocyclic compound of formula (II).

Preferably, however, alkaline catalyst such as tetraethylammonium chloride or tertiary amines are used in the manufacture of dialcohols of formula (I) in which the sum of m and n is 2. It is however also possible successfully to employ alkali halides such as lithium chloride or sodium chloride for this addition reaction; the reaction also takes place without catalysts.

In the manufacture of dialcohols of formula (I) in which the sum of m and n is greater than 2, it is preferable to start from the simple dialcohols of formula (I) in which m and n are each 1, and to add further alkene oxide to both OH— groups of this compound in the presence of acid catalysts.

Suitable acid catalysts for this addition reaction are especially Lewis acids, such as for example $AlCl_3$, $SbCl_5$, $SnCl_4$, $FeCl_3$, $ZnCl_2$, $BF_3$ and their complexes with organic compounds.

The mononuclear N-heterocyclic compounds of formula (II) used for the manufacture of the new alkene oxide addition products of formula (I) are above all hydantoin, hydantoin derivatives, barbituric acid, barbitric acid derivatives, uracil, uracil derivatives, dihydrouracil and dihydrouracil derivatives, and also parabanic acid.

Hydantoin and its preferred derivatives correspond to the general formula

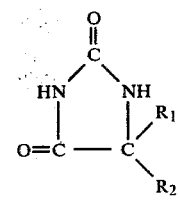

wherein $R_1$ and $R_2$ each denote a hydrogen atom or a lower alkyl residue with 1 to 4 carbon atoms, or wherein $R_1$ and $R_2$ together form a tetramethylene or pentamethylene residue. Hydantoin, 5-methyl-hydantoin, 5-methyl-5-ethylhydantoin, 5-n-propylhydantoin, 5-isopropylhydantoin, 1,3-diaza-spiro(4.5)-decane-2,4-dione, 1,3-diaza-spiro(4.4)-nonane-2,4-dione and preferably 5,5-dimethylhydantoin may be mentioned.

Barbituric acid and its preferred derivatives correspond to the general formula

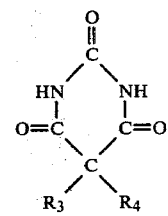

wherein $R_3$ and $R_4$ independently of one another each denote a hydrogen atom, an alkyl residue, an alkenyl residue, a cycloalkyl or cycloalkenyl residue or a substituted or unsubstituted phenyl residue.

The following may be mentioned: babituric acid, 5-ethylbarbituric acid, 5,5-diethylbarbituric acid, 5-ethyl-5-butylbarbituric acid, 5-ethyl-5-sec.-butylbarbituric acid, 5-ethyl-5-isopentylbarbituric acid, 5,5-diallylbarbituric acid, 5-allyl-5-isopropylbarbituric acid, 5-allyl-5-sec.-butylbarbituric acid, 5-ethyl-5(1'-methylbutyl)barbituric acid, 5-allyl-5(1'-methylbutyl)barbituric acid, 5-ethyl-5-phenylbarbituric acid and 5-ethyl-5(1'-cyclohexene-1-yl)barbituric acid.

Uracil and its preferred derivatives correspond to the general formula

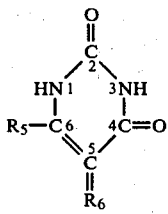

wherein $R_5$ and $R_6$ both denote hydrogen or one of the two residues denotes a hydrogen atom and the other residue denotes a methyl group.

Uracils of formula (V) are uracil itself; also 6-methyluracil and thymin (=5-methyluracil).

Dihydrouracil (=2,4-dioxo-hexahydropyrimidine) and its preferred derivatives correspond to the general formula:

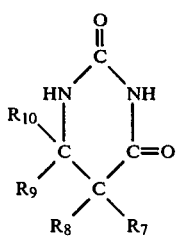

wherein $R_7$ and $R_8$ both denote a hydrogen atom or identical or different alkyl residues, preferably alkyl residues with 1 to 4 carbon atoms, and $R_9$ and $R_{10}$ independently of one another each denote a hydrogen atom or an alkyl residue.

Preferably, in the above formula, the two residues $R_7$ and $R_8$ denote methyl groups, $R_9$ denotes a hydrogen atom or a lower alkyl residue with 1 to 4 carbon atoms and $R_{10}$ denotes a hydrogen atom. The following may be mentioned: 5,6-dihydrouracil, 5,5-dimethyl-5,6-dihydrouracil (2,4-dioxo-5,5-dimethylhexahydropyrimidine) and 5,5-dimethyl-6-isopropyl-5,6-dihydrouracil (2,4-dioxo-5,5-dimethyl-6-isopropylhexahydropyrimidine).

The new diols are useful as intermediates and can be used like aliphatic diols for the preparation of polymers, such as polyesters or polyurethanes, or for the preparation of diglycidylethers, which resins can be used as e.g. molding compositions, adhesives, coatings, films and laminates having valuable properties.

EXAMPLE 1

1,3-Di($\beta$-hydroxy-n-propyl)-5,5-dimethylhydantoin

A mixture of 217 g of 5,5-dimethylhydantoin (1.695 mols) 3.61 g of lithium chloride (5 mol percent) and 560 ml of dimethylformamide is stirred at 50° C. 230 g of propene oxide (propylene oxide) (3.955 mols) are added dropwise to the clear solution over the course of 4 hours, 50°–55° C. The reaction is slightly exothermic. After the dropwise addition, the temperature is slowly raised to 90° C. After 5 hours at 90° C. the dimethylformamide is distilled off in a waterpump vacuum and thereafter the product is dried to constant weight at 100° C. and 0.1 mm Hg. 415 g of a pale yellow highly viscous oil (100% of theory) are obtained. The crude product is distilled at 0.1 to 0.2 mm Hg and 170°–172° C.: 386.0 g yield of pure material (93.5% of theory). On cooling the 1,3-di($\beta$-hydroxy-n-propyl)-5,5-dimethylhydantoin solidifies to give white crystals of melting point 65°–67° C. The elementary analysis shows 11.81% N (calculated, 11.47% N), and the molecular weight was determined by vapour pressure osmometry to be 247 (theory 244). The infrared spectrum shows the absence of N-H-amide frequencies at 3.1 to 3.2$\mu$ and the presence of C—OH frequencies at 2.90$\mu$.

EXAMPLE 2

1,3-Di($\beta$-hydroxy-n-propyl)-5,5-diethylbarbituric acid 40.7 g (0.7 mol) of propene oxide are added dropwise over the course of 1 hour to a mixture of 55.3 g of 5,5-diethylbarbituric acid (0.3 mol), 2.77 g of tetraethylammonium chloridde (5 mol percent) and 400 ml of dimethylformamide at 35° C. whilst stirring. Thereafter the mixture is gradually heated to 100° C. After 7 hours' stirring at 100° C. the mixture is worked-up in accordance with example 4. 92.5 g of crude 1,3-di($\beta$-hydroxy-n-propyl)-5,5-diethylbarbituric acid (99.5% of theory) are obtained. The product boils at 138°–148° C. under 0.08 mm Hg; 75.2 g or pure product (80% of theory) are obtained.

| Elementary analysis: | found: | calculated: |
|---|---|---|
| | 55.54% C | 55.98% C |
| | 8.03% H | 8.05% H |
| | 9.44% N | 9.32% N |

The IR (infrared) and H—NMR (nuclear magnetic resonance) spectrum can be reconciled with the following structure:

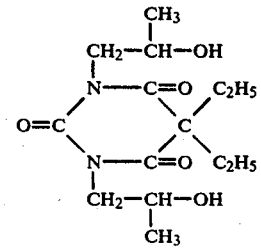

EXAMPLE 3

1,3-Di($\beta$-hydroxyethyl)-5,5-dimethylhydantoin

A solution of 48.5 g of ethene oxide (ethylene oxide) (1.1 mols) in 200 ml of dimethylformamide, cooled to about 5° C., is allowed to run into a mixture of 64.2 g of 5,5-dimethylhydantoin (0.5 mol), 4.15 g of tetraethylammonium chloride and 100 ml of dimethylformamide at room temperature. The mixture is gradually heated to 50°–60°0 C., whereupon the reaction starts with evolution of heat. After the exothermic reaction the mixture is stirred for a further 3 hours at 90° C. Working-up takes place as in example 1. 108.0 g of a viscous oil (99.7% of theory) are obtained. Purification takes place by vacuum distillation (boiling point $_{0.3}$=185°–186° C.), and the pure 1,3-di($\beta$-hydroxyethyl)-5,5-dimethylhydantoin is obtained in 86.8% yield. The product solidifies to give colourless small crystals which melt at about 40° C.

| Analytical data: | found: | calculated: |
|---|---|---|
| | 49.54% C | 49.99% C |
| | 7.39% H | 7.46% H |

| Analytical data: | found: | calculated: |
|---|---|---|
| ($M_{osmometric}$) | 212 | 216 ($M_{theory}$) |

EXAMPLE 4

1,3-Di(β-hydroxyethyl)-5-phenyl-5-ethylbarbituric acid 116.2 g of 5-phenyl-5-ethylbarbituric acid (0.5 mol) and 4.14 g of tetraethylammonium chloride (5 mol percent) in 300 ml of dimethylformamide were reacted with 54.9 g of ethene oxide in 250 ml of dimethylformamide in accordance with example C.

160.0 g of crude 1,3-di(β-hydroxyethyl)-5-phenyl-5-ethylbarbituric acid (100% of theory) are obtained. The product is purified by distillation (boiling point $_{0.3}$=220°–221° C.); 139 g (corresponding to 86.8% of theory) of pure substance are obtained. On cooling the substance crystalises; melting point =107°–109° C.

| Analytical data: | found: | calculated: |
|---|---|---|
| | 59.72% C | 59.99% C |
| | 6.41% H | 6.29% H |
| | 9.03% N | 8.75% N |

EXAMPLE 5

1,3-Di(β-hydroxyethoxyethoxyethyl)-5,5-dimethylhydantoin

A clear colourless solution is prepared at 60° C. from 108.1 g of 1,3-di(β-hydroxyethyl)-5,5-dimethylhydantoin (0.5 mol) [manufactured according to example 3], 500 ml of dioxan and 2 ml of a 47% strength boron trifluoride-diethyl etherate solution in diethyl ether. 88.1 g of ethene oxide (about 2 mols) are introduced into this solution over the course of 2 hours and 20 minutes. Here the procedure followed is to pass a constant ethene oxide gas stream of such strength into the solution that practically all the ethene oxide is absorbed. The amount of the ethene oxide introduced is continuously controlled by means of a suitable gas flow meter (rotameter). The reaction is weakly exothermic so that after removing the external heating the temperature of mixture rises about 10 degrees to 70° C. After stopping the stream of ethene oxide the mixture is cooled to 15° C. and treated with 15 ml of 50% strength sodium hydroxide solution. The mixture is filtered and the clear, amber-coloured solution is concentrated on a rotational evaporator (60°–80° C., 15 mm Hg) and thereafter treated at 80° C./0.1 mm Hg until constant weight is reached. An oil is obtained in quantitative yield, of which the IR (infrared) spectrum shows, in addition to the absorption due to the dimethylhydantoin, a strong OH absorption (2.92–3.02μ) and a very strong C-O-C absorption (8.9–9.4μ). The molecular weight is determined by vapour pressure osmometry to be M=394 (theory =392.5), and elementary analysis shows 51.7% C and 814% H (calculated: 52.0% C and 8.2% H).

A sample of this substance is dissolved in chloroform and extracted by shaking with a little 10% strength sodium hydroxide solution, and after separating off the aqueous phase the chloroform layer is dried over magnesium sulphate. Thereafter the product is precipitated from petroleum ether/cyclohexane, and the resulting light yellow oil is taken up in methylene chloride and treated until constant weight is reached (finally 60° C./0.1 mm Hg). The product purified in this way is practically a single substance according to a thin layer chromatogram. The H-NMR (nuclear magnetic resonance) spectrum and its integration show that the following 32 protons are present (overall formula: $C_{17}H_{32}N_2O_8$):

| | | |
|---|---|---|
| 6 methyl protons | at δ = | 1.40 |
| 2 C-OH protons | at δ about | 3.55 |
| 24 methylene protons | at δ about | 3.65 |

Since the addition of the ethene oxide presumably occurs statistically on both sides of the 1,3-di(β-hydroxyethyl)-5,5-dimethylhydantoin, the presence of essentially the following structure must be assumed on the basis of the results quoted:

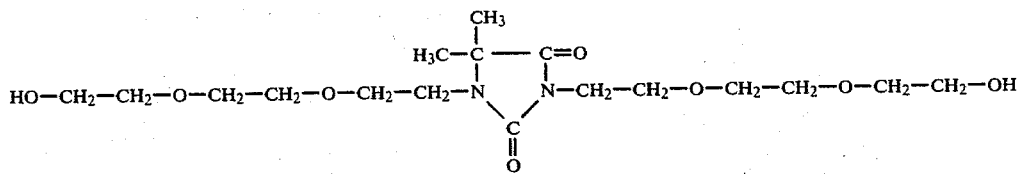

EXAMPLE 6

1,3-Di-(β-hydroxyethyl)-5,5-dimethyl-6-isopropyl-5,6-dihydrouracil

A solution of 440.5 g of ethene oxide (10 mols) in 500 ml of dimethylformamide is added at 10° C., whilst stirring, to a suspension of 548 g of 2,4-dioxo-5,5-dimethyl-6-isopropylhexahydropyrimidine (=5,5-dimethyl-6-isopropyl-5,6-dihydrouracil) (3 mols), 3 liters of commercial dimethylformamide and 20.0 g of lithium chloride. This mixture is slowly and steadily heated to 90° C. over the course of 4.5 hours whilst stirring, whereby a slightly cloudy dark yellow solution is produced. The mixture is now stirred for a further 12 hours at 90° C. and subsequently cooled; the pH-value of the solution is 8. It is then neutralized with 25% strength sulphuric acid and filtered. The clear dark-coloured solution is concentrated on a rotational evaporator at 80° C. under a waterpump vauum; thereafter traces of easily volatile constituents are removed at 80° C. under 0.1 mm Hg.

810 g of a dark highly viscous substance (10% of theory) are obtained. For purification, the substance is subjected to a high vacuum distillation. 630.4 g of distillate (77.8% of theory, relative to dihydrouracil derivative employed) of melting point 183°–188° C. at 0.25–0.30 mm Hg are obtained.

The elementary analysis, the infrared sepctroscopy and the nuclear resonance spectroscopy show that the substances produced in this way is the desired 1,3-di-(β-hydroxyethyl)-5,5-dimethyl-6-isopropyl-5,6-dihydrouracil.

| Elementary analysis: | found: | calculated: |
|---|---|---|
| | 57.45% C | 57.33% C |
| | 8.85% H | 8.88% H |
| | 10.32% N | 10.29% N |

The infrared spectrum, through the absence of the NH-frequencies and through the presence of, inter alia, the following absorptions shows that the reaction takes place as desired:

2.94μ (OH), 5.86μ+6.04μ(C=O), 9.50μ (C—O).

The nuclear magnetic resonance spectrum (60 Mc H-NMR, recorded in deuterochloroform no longer shows any signals for Co—NH— grouping, and shows, through a quartet at δ=0.75; 0.85; 0.99; 1.11 (CH-CH₃), through a doublet at δ=1.26 and 1.33 ([CH₃]₂=C), through a septet at

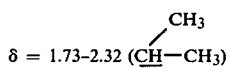

and through a further 11 protons at δ=3.0–4.4, that the following structure applies:

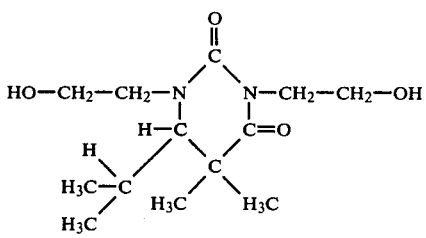

EXAMPLE 7

1,3-Di-(β-hydroxypropyl)-5,5-dimethyl-6-isopropyl-5,6-dihydrouracil

A suspension is prepared from 548 g of 2,4-dioxo-5,5-dimethyl-6-isopropyl-5,6-dihydrouracil, 3.5 liters of commercial dimethylformamide and 20.0 g of lithium chloride. The mixture is warmed to 40° C. and 581.0 g of propene oxide (10 mols) are uniformly added dropwise over the course of 3 hours with good stirring. This mixture is then warmed to 80° C. over the course of 1 hour and stirred at this temperature for 6 hours. The reaction mixture is subsequently cooled and filtered. The clear pale yellow filtrate is concentrated at 100° C. under a waterpump vacuum and is subsequently treated at 100° C. under 0.07 mm Hg until constant weight is reached. 742 g of a slightly orange-coloured, highly viscous, substance are obtained (82.7% of theory).

The nuclear magnetic resonance spectrum (60 Mc H-NMR, recorded in deuterochloroform) shows, through signals at δ=0.70; 0.81 (both split) and δ=0.95; 1.07; 1.14; 1.25 and 1.38; and also through a multiplet at δ=1.60-2.20; at δ=2.80-3.20 and at δ=3.20-4.20, that the desired reaction has occurred. Equally, the infrared spectrum shows, through the absence of NH- frequencies and through the OH- frequencies appearing at 2.97μ, that the new diol essentially has the following structure:

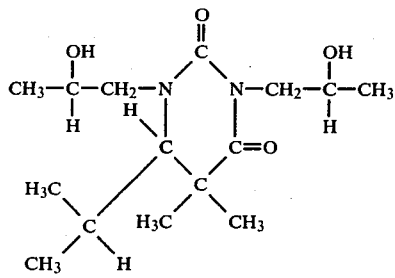

EXAMPLE 8

1,3-Di-(β-hydroxyethyl-polyethoxyethyl)-5,5-dimethylhydantoin 21.6 g of 1,3-di-(β-hydroxyethyl)-5,5-dimethylhydantoin (manufactured according to example 3) (0.1 mol) are dissolved in 600 g of anhydrous dioxan and stirred at 65° C. 1.5 ml of 47% strength ethereal boron trifluoride-diethyl etherate solution are added and 264.3 g of ethylene oxide (6.0 mols)=134.4 liters are introduced in the gas form over the course of 4 hours, whilst stirring. The ethylene oxide stream is metered by means of a gas flow meter (rotameter). The reaction is exothermic, so that heating can be dispensed with; occasionally it is even necessary to cool slightly with ice water in order to maintain the reaction temperature of about 65° C. The mixture is left to stand overnight and 18 ml of 1 N NaOH are stirred in so as to neutralise the boron trifluoride. The cloudy solution is filtered and the water-clear, colourless filtrate is concentrated on a rotational evaporator under 20 mm Hg. Thereafter volatile constituents are removed at 80° C./0.08 mm Hg. 218 g of a colourless oil of low viscosity are obtained, corresponding to an ethylene oxide uptake of 196.4 g (=4.466 mols). The analyses show the following results: the proton magnetic resonance spectrum (60 Mc H-NMR, recorded in CDCl₃ at 35° C.) essentially only still shows the signals for C—CH₃ at δ'=1.30 and a very intense multiplet at about δ=3.62, due to the —(CH₂—CH₂—O)$_n$— groups. Elementary analysis shows the following values: 53.3% C., 8.9% H and 1.6% N. This means that on average about 20-23 ethylene oxide units are bonded to each N atom of the hydantoin. Gel permeation analysis shows a molecular weight distribution according to which the distribution function has a maximum at about 20-24 ethylene oxide units per N atom, corresponding to a molecular weight of about 2000-2500.

The average molecular weight was determined by vapour pressure osmometry to be 1100-1200, and this value is confirmed by the molecular weight distribution curve of the gel permeation analysis.

EXAMPLE 9

1,3-Di-(β-hydroxy-n-propyl)-5-isopropylhydantoin

A mixture of 995.0 g of 5-isopropylhydantoin (7 mols), 2000 ml of dimethylformamide and 14.8 g of lithium chloride is stirred at 50° C. 1220 g of propene oxide (21 mols) are slowly added dropwise over the course of 6 hours. Thereafter the temperature is gradually raised to 70° C. and after a total of 15 hours the reaction mixture is allowed to cool. It is adjusted to pH=7 with a few drops of 2 N H₂SO₄ and the pale yellow solution is filtered. The solution is completely concentrated at 90° C. bath temperature on a rotational evaporator under a waterpump vacuum and is subsequently treated at 90° C./0.1 mm Hg until constant weight is reached. 1654.5 g of a pale yellow highly viscous product (91.7% of theory) are obtained.

The product can be purified by vacuum distillation; at 158° C., under 0.08-0.1 mm Hg, 76% of the material employed distil as a colourless oil which slowly crystallises.

The infrared spectrum shows, through the absence of NH absorptions and through the presence of very intense OH absorptions at 2.93μ, that the desired diol has been produced.

The proton magnetic resonance spectrum also shows that the resulting product mainly consists of 1,3-di-(β-hydroxy-n-propyl)-5-isopropylhydantoin.

EXAMPLE 10

1,3-Di-(β-hydroxy-n-propyl)-5,5-dimethylhydantoin

A mixture of 128.1 g of 5,5-dimethylhydantoin (1 mol), 1.0 g of lithium chloride and 224 g of 1,3-di-(β-hydroxy-n-propyl)-5,5-dimethylhydantoin (manufactured according to example A) is stirred at 120° C. A clear solution is thereby produced. 133.9 g of propene oxide (2.3 mols) are slowly added dropwise over the course of 1 hour with good stirring. The temperature hereupon drops down to 60° C. After the dropwise addition the mixture is stirred for a further 6 hours at 70° C. A total of 461.1 g of crude 1,3-di-(β-hydroxy-n-propyl)-5,5-dimethylhydantoin (98.3% of theory) is obtained, agreeing in its properties with the product described in example 1.

EXAMPLE 11

1,3-Di-(β-hydroxyethyl)-5,5-dimethylhydantoin

A mixture of 128.12 g of 5,5-dimethylhydantoin, 1.06 g of lithium chloride and 193.73 g of ethylene glycol carbonate is heated from 118° C. to 190° C. over the course of 5 hours whilst stirring. The reaction is slightly exothermic and from about 130° C. onwards a vigorous evolution of $CO_2$ starts. The mixture is stirred for a further 1.1 hours at 190° C., and the $CO_2$ evolution and hence the reaction are then complete. 1,3-Di-(β-hydroxyethyl)-5,5-dimethylhydantoin, having the same properties as the product described in example 3, is produced in quantitative yield: boiling point $_{0.1}$=174°-177° C. The nuclear resonance spectrum can be reconciled with this structure and no longer shows any signals for NH groups.

EXAMPLE 12

1,3-Di-(β-hydroxy-n-propyl)-5,5-diethylhydantoin

A solution of 125.0 g of 5,5-diethylhydantoin (0.8 mol), 300.0 g of dimethylformamide and 2.00 g of lithium chloride is stirred at 52° C. 128.0 g of propene oxide (2.2 mols) are added dropwise over the course of 2½ hours. Stirring is then continued for 5 hours at 85°-90° C. The reaction mixture is adjusted to pH=7 with 2-3 drops of 25% strength sulphuric acid, and is filtered. The clear solution is concentrated on a rotational evaporator at 80° C. bath temperature, under a waterpump vacuum, and is subsequently treated under a high vacuum (0.1 mm Hg) at 80° C. until constant weight is reached.

206.0 g of a yellow, viscous, product (95.0% of theory), which can be purified by distillation, are obtained. At 179°-181° C./0.15 mm Hg 80.0% of the crude product employed distil as a colourless liquid. The infrared spectrum shows inter alia through the absence of the NH absorptions and through strong OH bands at 2.89μ that the reaction has followed the desired course. The proton magnetic resonance spectrum (60 Mc H-NMR, recorded in deuterochloroform) shows inter alia through the signals for 2×(CH₃—CH₂) (multiplet at δ=0.68-1.02), for 2×(CH₃—CH—OH) (doublet with fine structure at δ=1.18 to 1.33) and for 2×CH₃—CH₂— (δ=2.63-2.05) that the product has the following formula:

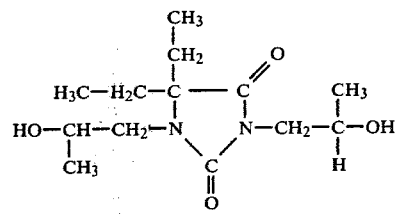

EXAMPLE 13

1,3-Di-(β-hydroxy-n-propyl)-5-ethyl-5-methylhydantoin

A mixture of 256.3 g of 5-ethyl-5-methylhydantoin (1.805 mols), 675 ml of dimethylformamide and 4.51 g of lithium chloride is stirred at 50° C. 288.0 g of propene oxide (4.96 mols) are slowly added dropwise over the course of 2 hours. Thereafter the temperature is gradually raised to 90° C. over the course of 10 hours. The reaction mixture is brought to pH=7 with 4 drops of 2 N hydrochloric acid, filtered and concentrated on a rotational evaporator at 90° C. bath temperature, under a waterpump vacuum. It is then treated at 90° C. under 0.1 mm Hg until the weight remains constant. 465 g of a clear pale yellow product (99.5% of theory) are obtained.

Purification is carried out by high vacuum distillation. A colourless highly viscous substance which distils at 145°-148° C./0.06 mm Hg is obtained in 78% yield of pure substance, relative to 5-ethyl-5-methylhydantoin employed.

Elementary analysis gives the following values:

| found: | calculated: |
|---|---|
| 55.63% C | 55.79% C |
| 8.66% H | 8.58% H |
| 10.82% N | 10.85% N |

The infrared spectrum further shows inter alia through an intense OH band at 3485 cm$^{-1}$ that the reaction has succeeded.

The nuclear magnetic resonance spectrum (60 Mc H-NMR, recorded in CDCl₃) furthermore shows, through the following signals, that the structure given below is present:

| 3 Protons at δ = 0.62 0.77 0.88 | (triplet): | —CH₂—CH₃ |
|---|---|---|
| 6 Protons at δ = 1.15 | (doublet with fine structure) | H<br>\|<br>HO—C—CH₃<br>\| |

-continued

3 Protons at δ = 1.42 (singlet)

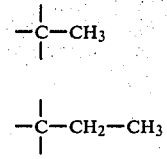

2 Protons at δ = 1.52–2.0 (quartet with fine structure)

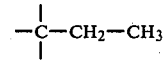

Remaining protons at δ = 2.85–4.25

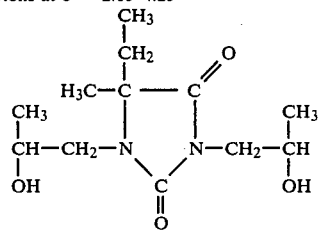

EXAMPLE 14

1,3-Di-(β-hydroxyethyl)-5,5-diphenylhydantoin 504.6 g (2.0 moles) of 5,5-diphenylhydantoin and 6.35 g of LiCl were added to 1000 ml of N,N-dimethylformamide and the mixture was stirred at 65° C. A solution of 194 g (4.4 moles) of ethylene oxide in 500 ml of N,N-dimethylformamide was added dropwise to this clear solution over the course of 2 hours. After completion of the addition and the exothermoc reaction has died down, the temperature was raised to 100° C. with stirring over the course of 1½ hours and the reaction was allowed to continue for a further 3 hours at 100° C. The solution was then cooled to 25° C., adjusted to a pH of 7 with dilute sulphuric acid, filtered, and the dimethyl formamide was distilled off at 80°–100° C. under a pressure of 15–25 Torr. The residual solution was poured into 4 liters of water and filtered. The residue was dried to constant weight at 90° C./0.5 Torr. Yield: 655.1 g of the desired crude product in the form of colourless crystals ( ≙ 96.2% of theory).

The crude product was purified by recrystalling it from methanol (substance: solvent = 1/1.5). Colourless crystals with a melting point of 140.3° C. are obtained.

| Elementary analysis: | found | estimated for $C_{19}H_{20}N_2O_4$ |
|---|---|---|
| | 66.99% C | 67.04% C |
| | 5.91% H | 5.92% H |
| | 8.20% N | 8.23% N |

Both the 60 MC-HNMR spectrum and the mass spectrum are in agreement with the following structure:

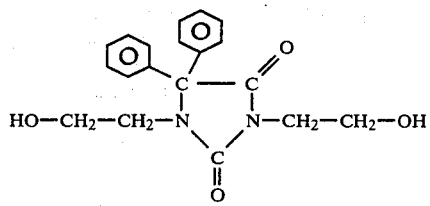

This compound has a sufficient thermal stability in order to use it for polycondensation reaction. The results of the experiment concerning the thermal stability are indicated in the table I.

COMPARISON EXAMPLE

Manufacture of 1,3-dihydroxymethyl-5,5-diphenylhydantoin

In accordance with Example 5 of U.S. Pat. No. 3.595.862, 50.4 g (0.2 mole) of 5,5-diphenylhydantoin were suspended in a mixture of 50 ml of dioxan and 200 ml of water. To this suspension was added 88 ml of 37% aqueous formaldehyde solution and 10 ml of triethanolamine and the mixture was stirred for 7 hours at 92°–98° C. The resultant clear, colourless solution was cooled to 25° C., adjusted to a pH of 1 and extracted with ether (3×100 ml). The ethereal solution was washed with 50 ml of saturated saline solution and dried over anhydrous sodium sulphate. The ether was distilled off under reduced pressure (bath temperature 40° C.) and the 1,3-di-(hydroxymethyl)-5,5-diphenylhydantoin is obtained as an oil in a yield of 63.1 g (99.8% of theory).

Proof of thermal stability

The thermal stability was determined by treating 7.95 g of 1,3-di-(hydroxymethyl)-5,5-diphenylhydantoin and 1,3-di-(hydroxyethyl)-5,5-diphenylhydantoin respectively in separate glass dishes at 150° C. and 60–70 Torr over the course of 14 hours in the same drying oven, which corresponds to very mild melt-polycondensation conditions. The results of this experiment are reported in the following table:

Table I

| 7.95 g of: | 1,3-di-(hydroxymethyl)-5,5-diphenylhydantoin (U.S. Pat. 3.595.862) | 1,3-di-(hydroxyethyl)-5,5-diphenylhydantoin (according to the invention |
|---|---|---|
| weight loss after 14 hours at 150° C./60–70 Torr | 1.67 g (formaldehyde and traces of solvent) | 0.01 g (traces of solvent) |
| appearance of the treated product | solid glass, light brown | colourless, solidified glass |
| composition of the treated product | according to NMR spectrum and melting point (294.1° C.): 5,5-diphenylhydantoin | according to NMR spectrum and melting point (140° C.): 1,3-di-(2'-hydroxyethyl)-5,5-diphenylhydantoin |

Whereas the 1,3-dihydroxymethyl-5,5-diphenylhydantoin under the reaction conditions applied split back quantitatively into the starting materials, the 1,3-di-hydroxyethyl-5,5-diphenylhydantoin remained unchanged after this treatment and can therefore be used for polycondensation reactions.

APPLICATION EXAMPLE

(a) Preparation of 1,3-di-(β-glycidyl-n-propyl)-5,5-dimethylhydantoin

A mixture of 660 g 1,3-di-(β-hydroxy-n-propyl)-5,5-dimethylhydantoin (1.852 mols) (manufactured according to example 1), 3268 g of epichlorhydrin (35.3 mols) and 14.68 g of tetraethylammonium chloride is stirred for 1½ hours at 90° C. and subsequently cooled to 60° C. 612 g of 50% strength sodium hydroxide solution are slowly added dropwise at 60° C. over the course of 2 hours with vigorous stirring, and at the same time the water present in the reaction mixture is continuously removed by ezeotropic circulatory distillation under 60–90 mm Hg. After completion of addition of the alkali solution azeotropic distillation is continued for a further 20 minutes. The sodium chloride produced in the reaction is then separated off by filtration and rinsed with 100 ml of epichlorohydrin. The combined epichlorhydrin solutions are extracted by shaking with 300 ml of water. After separating off the aqueous phase, the organic phase is concentrated at 60° C./20 mm Hg and then treated at 60° C./0.08 mm Hg until the weight remains constant.

A resin of low viscosity, with an epoxide content of 5.61 equivalents/kg (100% of theory) is obtained in 94% yield (903 g). The viscosity of the resin at 20° C. is 630 cP and the total chlorine content 0.9%.

(b) Curing of 1,3-di-(β-glycidyloxy-n-propyl)-5,5-dimethylhydantoin

A homogeneous mixture of 196.7 g of the 1,3-di-(β-glycidyloxy-n-propyl)-5,5-dimethylhydantoin and 144.0 g of hexahydrophthalic anhydride is prepared at 55° C. This mixture is poured into moulds pre-warmed to 80° C., having the following dimensions: (a) 14×4.2×1.0 cm at about 0.1 mm wall thickness for mechanical tests; (b) 13.0×13.0×0.4 or 0.2 cm at about 4.0 mm wall thickness for electrical tests.

The curing takes place in 2 hours at 80° C. and 2 hours at 120° C. and 15 hours at 150° C. The clear, pale yellow, mouldings thus obtained have the following properties:

| | |
|---|---|
| Flexural strength (VSM 77,103) | 14.75 kp/mm$^2$ |
| Deflection (VSM 77,103) | 10.0 mm |
| Impact strength (VSM 77,105) | 12.25 cmkp/cm$^2$ |
| Heat distortion point according to Martens (DIN 53,358) | 75° C. |
| Water absorption (4 days 20° C.) | 0.48% |
| Breakdown voltage (VDE 0303) | 236 kV/cm |
| Tracking resistance (VDE 0303), level | KA3c |
| Arcing resistance (VDE 0303), level | L4 |
| Specific resistance (VDE 0303), 20° C. | $4.7 \cdot 10^{16} \, \Omega \cdot cm$ |
| Dielectric constant (DIN 53,483), 20° C. | 3.50 |
| Dielectric loss factor tg δ (50 Hz; DIN 53,483), 20° C. | 0.005 |

We claim:
1. A compound 1,3-di-(Beta-hydroxyethyl)-5,5-dimethylhydantoin which is a crystalline solid.

* * * * *